(12) United States Patent
Panczner

(10) Patent No.: US 6,559,428 B2
(45) Date of Patent: May 6, 2003

(54) INDUCTION HEATING TOOL

(75) Inventor: Herbert Scharner Panczner, Pattersonville, NY (US)

(73) Assignee: General Electric Company, Schenectady, NY (US)

(*) Notice: Subject to any disclaimer, the term of this patent is extended or adjusted under 35 U.S.C. 154(b) by 289 days.

(21) Appl. No.: 09/760,298

(22) Filed: Jan. 16, 2001

(65) Prior Publication Data

US 2002/0092845 A1 Jul. 18, 2002

(51) Int. Cl.[7] .............................. H05B 6/14; H05B 6/42
(52) U.S. Cl. .................. 219/615; 219/635; 219/672; 219/659; 219/677
(58) Field of Search .................. 219/615, 616, 219/602, 632, 659, 635, 672, 673, 674, 675, 677

(56) References Cited

U.S. PATENT DOCUMENTS

| | | | | | |
|---|---|---|---|---|---|
| 2,759,085 A | * | 8/1956 | Van Iperen | ............ | 219/677 |
| 3,204,074 A | * | 8/1965 | Hunting, Jr. | ............ | 219/677 |
| 3,238,346 A | * | 3/1966 | Savko | ............ | 219/659 |
| 3,365,563 A | * | 1/1968 | Basinger | ............ | 219/615 |
| 5,026,956 A | * | 6/1991 | Busch | ............ | 219/659 |

\* cited by examiner

*Primary Examiner*—Philip H. Leung
(74) *Attorney, Agent, or Firm*—Nixon & Vanderhye

(57) ABSTRACT

An induction brazing tool includes a pair of induction coil components each having a linear extension and a semi-circular coil at one end. A distal end of each component remote from the semi-circular coil includes a flange for connecting the tool to an induction brazer. The components are formed of electrical conductive hollow copper tubing. The opposite end of each component includes a flange for bolting the components to one another. Nipples are provided the ends of the coil portions and a flexible hose interconnects the nipples. A braid of electrical conductive material also connects the nipples. In use, the components are opened to form a clamshell configuration, disposed about parts to be brazed and bolted together and to the brazer. By flowing electrical current and cooling water along the tool, a brazed joint is effected.

16 Claims, 2 Drawing Sheets

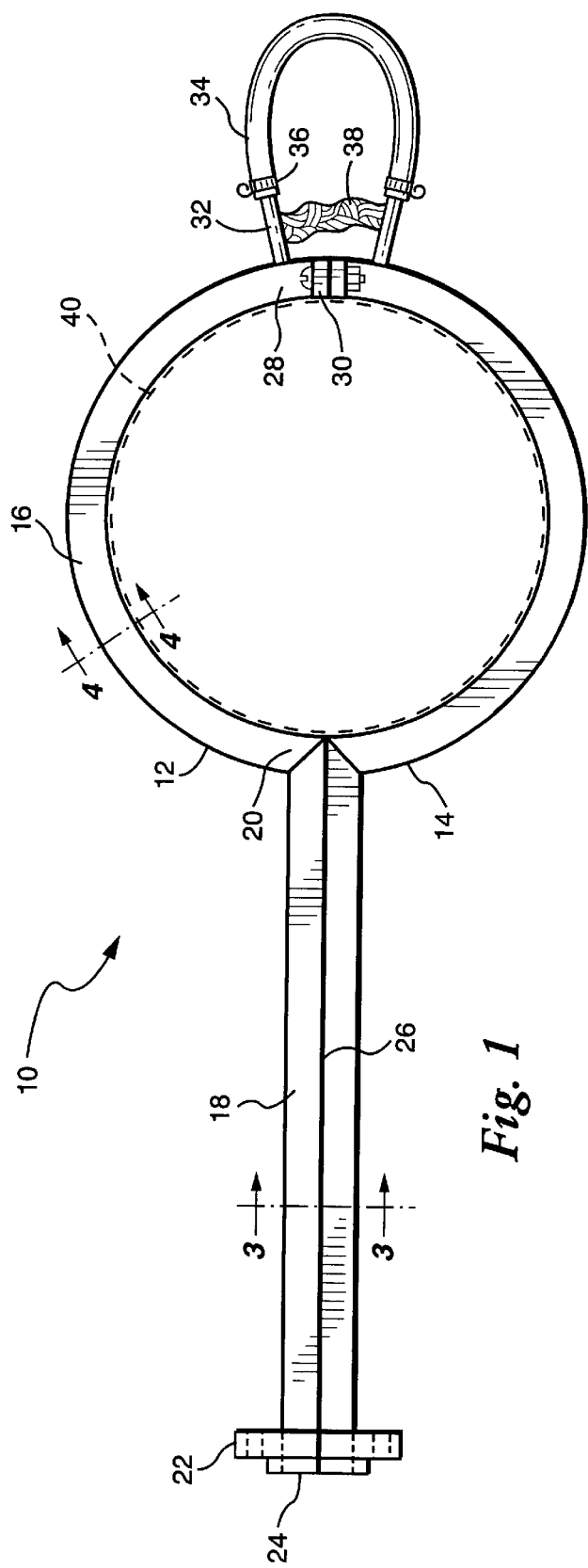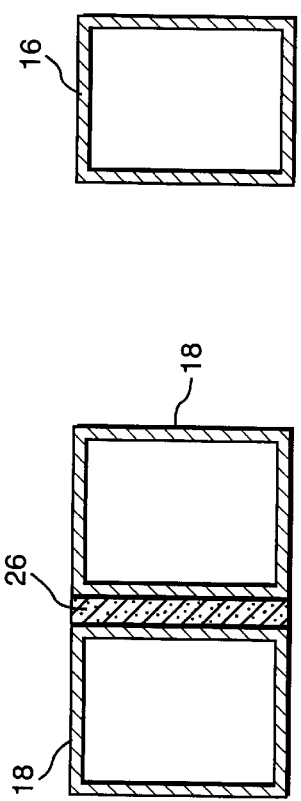

INDUCTION HEATING TOOL

BACKGROUND OF THE INVENTION

The present invention relates generally to a tool for induction heating of components to be joined one to the other and particularly relates to an induction heating coil for brazing copper components at electrical generator locations difficult to access and braze by conventional brazing tools.

Brazing component parts together is an old and tried method of joining the parts. Typically, brazing is accomplished by using an open flame, for example, propane, and an oxygen gas in conjunction with brazing filler and flux materials. While such brazing method and tools are satisfactory for original equipment manufacture, oftentimes there is a need for brazing parts to one another in cramped and confined spaces where the use of an open flame cannot safely be utilized. For example, in a power generating facility, liquid cooled high voltage bushing components are located in the electrical generator lower frame extension. Field brazing of these components is oftentimes unacceptable in the power generating facility. Accordingly, there is a need for a brazing tool for induction heating of the parts to be brazed to one another which can be used in cramped, confined spaces, reused for multiple applications, and used for original equipment as well as field repair applications.

BRIEF SUMMARY OF THE INVENTION

In accordance with a preferred embodiment of the present invention, there is provided a tool for brazing application including an induction coil formed of a pair of induction coil components which are substantially similar to one another, i.e., substantially mirror images of one another. Each component includes a linear extension or leg, whose proximal end is coupled to a first end of a generally semi-circular induction coil portion. The opposite or second end of the semi-circular induction coil portion terminates in a flange such that the opposed induction coil components can be secured one to the other. The distal end of each extension has an adapter flange portion forming part of an adapter for securing the tool to an induction brazer for supplying electrical current and cooling water to the induction tool. In that manner, an induction coil extending a full 360° is formed having a specific diameter designed for a close fit about and used to join components of a particular diameter. The linear extensions lie parallel to one another along their lengths and have electrical insulating material therebetween. The induction coil components are preferably formed of hollow, electrical conductive, e.g., copper. Preferably, the tubes are rectilinear in cross-section.

At the opposite end of the tool and adjacent the juncture of the second ends of the semi-circular coil portions, there are provided a pair of nipples, one on each coil portion end. A flexible conduit, e.g., a hose, is attached to the nipples, whereby water flowing through the linear extension and semi-circular portion on one side of the tool traverses the joint between the components for flow through the semi-circular coil portion and linear extension of the other side of the tool. Additionally, an electrically conductive material, for example, a braid, interconnects the nipples or opposite sides of the semi-circular coil portions to one another to ensure electrical conductivity between the two component halves.

With the foregoing arrangement of the tool, the semi-circular component portions can be disposed on opposite sides of the parts to be brazed to one another and bolted to one another about the parts and to the brazer. The diameter of the semi-circular portions closely approximates the diameter of the parts to be brazed whereby high coupling efficiency with minimum applied power is provided while reaching and holding the brazing temperature. With the semi-circular portions of the brazing tool about the parts, the temperature is raised to the brazing temperature and the filler material, e.g., about 80% copper, 15% silver and 5% phosphorus, is applied to the parts. Other brazing alloys may be used. A cooling medium, e.g., water, is simultaneously supplied from the brazer through the tool to cool the tool during brazing. After brazing, the components are separated from one another by detaching the bolted connections at the semi-circular component portion end, as well as at the adapter end. The brazing tool is then opened, e.g., in a clamshell manner, and removed from about the brazed parts for reuse and reapplication to other parts required to be brazed to one another. It will be appreciated that the brazing tool is thus compact and can be utilized in confined spaces, for example, to braze the generator high voltage bushings and component parts thereof as necessary in a generator. Applications of the tool hereof to braze other parts in other environments are also within the scope hereof.

In a preferred embodiment according to the present invention, there is provided an induction coil for brazing comprising a pair of induction coil components, each component including a generally semi-circular induction coil portion and a generally linear extension extending from a first end of the semi-circular induction coil portion, each coil portion and extension being formed of a hollow, electrical conductive material for flowing a cooling medium and conducting electricity between an end of the extension, along the extension, and through the semi-circular induction coil portion to a second end of the semi-circular induction coil portion opposite the first end, means for releasably securing the components to one another such that the semi-circular induction coil portions form a generally circular coil for surrounding workpieces to be brazed to one another and with the extensions in opposed registration with one another and a bypass conduit for hydraulically connecting the coil portions to one another adjacent the second end thereof.

In a further preferred embodiment according to the present invention, there is provided an induction coil for brazing comprising a pair of induction coil components, each component including a generally semi-circular induction coil portion and an extension extending from a first end of the semi-circular induction coil portion, each coil portion and extension being formed of a hollow, electrical conductive material for flowing a cooling medium and conducting electricity between an end of the extension, along the extension, and through the semi-circular induction coil portion to a second end of the semi-circular induction coil portion opposite the first end, the second ends of the semi-circular induction coil portions being closed, a releasable securing device for securing the components to one another adjacent the second ends thereof such that the semi-circular induction coil portions form a generally circular coil for surrounding workpieces to be brazed to one another and a bypass conduit for hydraulically connecting the coil portions to one another adjacent the second end thereof whereby the cooling medium may flow serially through one component and subsequently another component.

BRIEF DESCRIPTION OF THE DRAWINGS

FIG. 1 is a plan view of an induction brazing tool constructed in accordance with a preferred embodiment of the present invention and illustrated in a closed position about parts being brazed;

FIGS. 3 and 4 are cross-sectional views thereof taken generally about on lines 3—3 and 4—4 in FIG. 1, respectively.

DETAILED DESCRIPTION OF THE INVENTION

Figure 2:
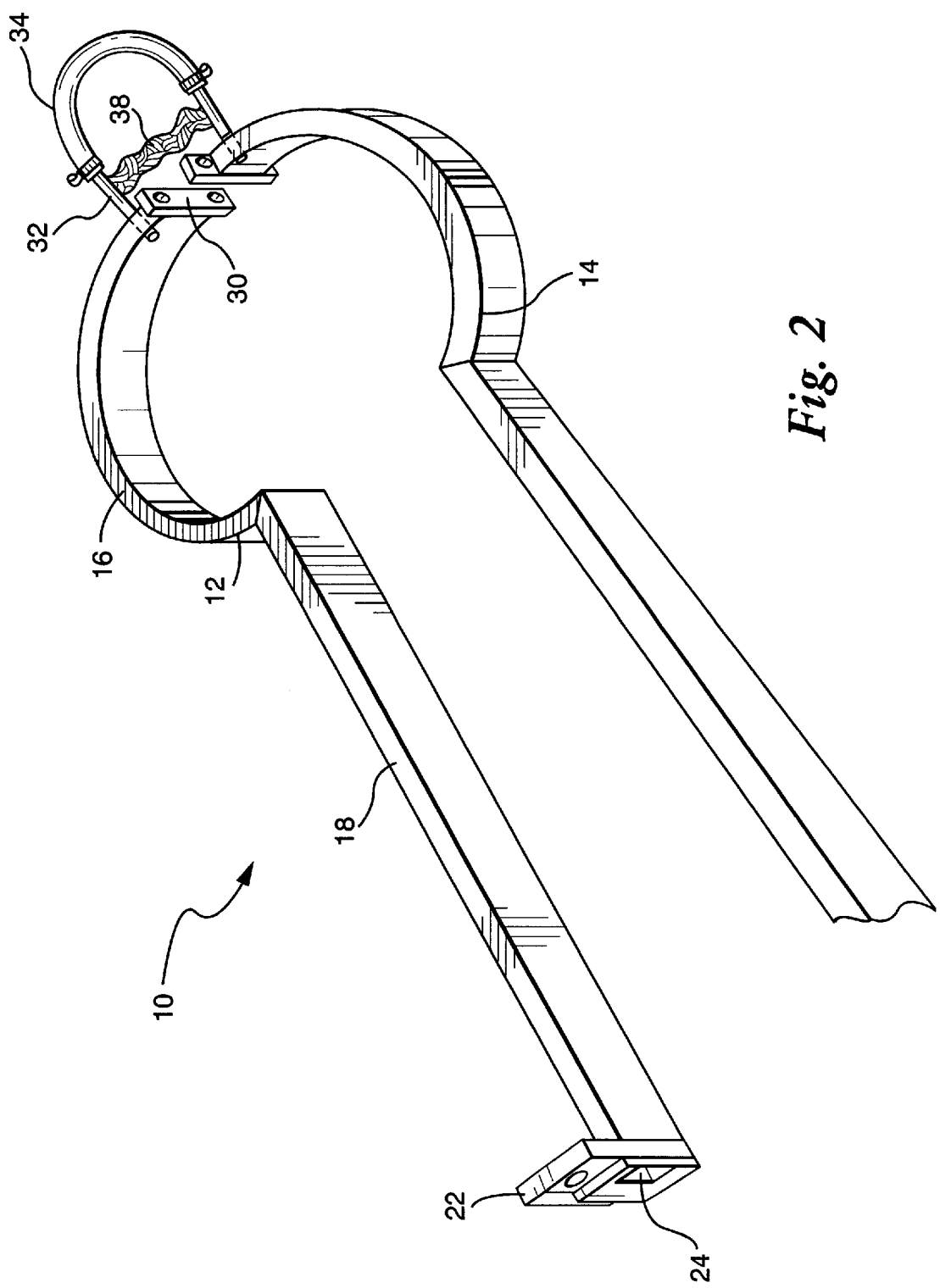
FIG. 2 is a perspective view of the brazing tool illustrated in FIG. 1 in an open position.

Referring now to the drawings, particularly to FIG. 1, there is illustrated an induction brazing tool constructed in accordance with a preferred embodiment of the present invention and generally designated 10. Tool 10 includes a pair of tool components, i.e., tool halves, 12 and 14 which comprise substantially mirror images of one another. Each component 12 and 14 includes a generally semi-circular induction coil portion 16 and a generally linear extension or leg 18 extending from a first end 20 of the semi-circular induction coil portion 16. The portion 16 and extension 18 are preferably formed of a hollow, electrically conductive material. As an illustrative example, portion 16 and extension 18 may each be formed of copper tubing having a rectilinear cross-section, with the tubing of portion 16 and extension 18 being connected to and in communication with one another. Each extension 18 terminates at its distal end in a flange portion 22 and an opening 24. The flanges 22 form an adapter at the end of the tool having bolt openings for securing the tool to an induction brazer, not shown, for supplying power to the tool. The tool 10 is also secured to the brazer such that a cooling medium, e.g., water, may be supplied to the tool through an opening 24 for flow along one extension 18 and coil portion of one component 16 and returned through the coil portion 16, extension 18 and opening 24 of the other component.

The copper tubing of the extensions and coil portions are illustrated in FIGS. 3 and 4, respectively. In FIG. 3, the tubing of the extensions 18 are separated one from the other by an electrical insulating material 26, for example, Nomex. The opposite or second end of each coil portion 16 of the end 28 preferably terminates in a flange 30 having bolt holes. The components 12 and 14 thus having mating flanges 30 which may be bolted one to the other. It will be appreciated that other devices for securing the components 12 and 14 may be used such as releasable clamps.

The second end 28 of each coil portion 16 also includes a connection, i.e., a nipple 32 in communication with the water flow passage within the coil portion 16. So that the water flowing from coil portion 16 of one component may flow into the coil portion 16 of the other component, a bypass conduit, preferably flexible tubing 34, for example, a rubber hose section, is releasably secured at opposite ends to the nipples 32, spanning the joint between the second ends 28 of the coil portions 16. Hose clamps 36 are provided for releasably securing the tubing 34 to the nipples 32. Additionally, a braid 38 of electrically conductive material is releasably interconnected between the nipples 32 to ensure electrical connection between the coil portions 16 when the induction tool components 12 and 14 are secured one to the other with the coil portions 16 about the parts to be joined to one another. While the flanges 30 of the two components are bolted to and in electrical contact with one another, that contact may deteriorate through usage. Hence, the braid 38 ensures electrical contact.

It will be appreciated that the aforedescribed tool is compact and is thus usable and reusable in confined spaces for joining various parts to one another. For example, the high voltage bushings within a generator lower frame extension of an electrical generator may be induction-heated by this tool, notwithstanding the cramped and confined space of the housing for the bushings. Moreover, the diameters of the induction coil portions 16 are dimensioned for a close-fitting relation with the parts to be brazed to one another, thereby affording a high coupling efficiency with minimum power enabling the tool to quickly reach and hold brazing temperatures.

In use, the components 12 and 14 are separated one from the other at opposite ends, preferably leaving the braid 38 and tubing connected to those ends. The tool may thus be deployed in a generally clamshell configuration about the parts to be brazed such that the coil portions 16 can be disposed about the opposite sides of such parts. When located about the parts to be brazed, the portions 16 are joined to one another, for example, by bolting the flanges 30 to one another. Additionally, the adapter at the distal end of the extensions 18 is bolted to the induction brazer. With the tool situated on the parts to be brazed to one another, cooling water is supplied from the brazer through the hollow tubular material of the extension 18 and coil portion 16 of one component in series via the nipples 32 and tubing 14 through the extension and coil portion of the other component. Electrical current is also provided from the induction brazer. Filler material is also supplied to the parts to be brazed to one another, e.g., using a rod of such filler material, and the coil portions are brought to the brazing temperature, for example, 1200° F. When the brazing temperature is reached and maintained sufficiently to melt the filler and complete the brazed joint, the power and water flow are cut off. The tool 10 is then removed by unbolting the tool from the brazer and separating the components 12 and 14 from one another by unbolting the flanges 30. The resulting clamshell-type configuration is then removed from about the brazed parts.

It will be appreciated that the present tool may be used and reused in a safe manner, for example, in a power generating facility where cramped and confined quarters preclude the use of other types of tools for brazing. Also, by forming the coil portions in close-fitting relation about the parts to be joined, high coupling heating efficiency with minimum power input is provided. The tool, for example, can be repeatedly used to connect parts within the cramped spaces without the use of an open flame or oxygen gas and, hence, can be used safely and efficiently.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An induction coil for brazing comprising:
   a pair of induction coil components, each component including a generally semi-circular induction coil portion and a generally linear extension extending from a first end of the semi-circular induction coil portion;
   each said coil portion and said extension being formed of a hollow, electrical conductive material for flowing a cooling medium and conducting electricity between an end of said extension, along said extension, and through the semi-circular induction coil portion to a second end of the semi-circular induction coil portion opposite said first end;

means for releasably securing the components to one another such that said semi-circular induction coil portions form a generally circular coil for surrounding workpieces to be brazed to one another and with said extensions in opposed registration with one another; and a bypass conduit for hydraulically connecting the coil portions to one another adjacent said second end thereof.

2. A tool according to claim 1 including electrical insulation disposed between said extensions upon securement of the components to one another.

3. A tool according to claim 1 wherein each bypass conduit includes a pair of connections coupled to said semi-circular coil portions, respectively, and a flexible conduit portion coupled at opposite ends to said connections for flowing the cooling medium from one component to another of said components.

4. A tool according to claim 1 wherein said securing means includes flanges adjacent the second ends of said semi-circular coil portions and bolts for releasably securing said flanges to one another.

5. A tool according to claim 1 wherein distal ends of said extensions include flanges for releasable securement to an induction brazer.

6. A tool according to claim 1 including a flexible conductive element extending between said coil portions for ensuring electrical conductivity between said coil portions.

7. A tool according to claim 1 including electrical insulation disposed between said extensions upon securement of the components to one another, each bypass conduit including a pair of connections coupled to said semi-circular coil portions, respectively, and a flexible conduit portion coupled at opposite ends to said connections for flowing the cooling medium from one component to another of said components.

8. A tool according to claim 7 including a flexible conductive element extending between said coil portions for ensuring electrical conductivity between said coil portions.

9. An induction coil for brazing comprising:

a pair of induction coil components, each component including a generally semi-circular induction coil portion and an extension extending from a first end of the semi-circular induction coil portion;

each said coil portion and said extension being formed of a hollow, electrical conductive material for flowing a cooling medium and conducting electricity between an end of said extension, along said extension, and through the semi-circular induction coil portion to a second end of the semi-circular induction coil portion opposite said first end, said second ends of the semi-circular induction coil portions being closed;

a releasable securing device for securing the components to one another adjacent said second ends thereof such that said semi-circular induction coil portions form a generally circular coil for surrounding workpieces to be brazed to one another; and a bypass conduit for hydraulically connecting the coil portions to one another adjacent said second end thereof whereby the cooling medium may flow serially through one component and subsequently another component.

10. A tool according to claim 9 including electrical insulation disposed between said extensions upon securement of the components to one another.

11. A tool according to claim 9 wherein each bypass conduit includes a pair of connections coupled to said semi-circular coil portions, respectively, and a flexible conduit portion coupled at opposite ends to said connections for flowing the cooling medium from one component to another of said components.

12. A tool according to claim 9 wherein distal ends of said extensions include flanges for releasable securement to an induction brazer.

13. A tool according to claim 9 including a flexible conductive element extending between said coil portions for ensuring electrical conductivity between said coil portions.

14. A tool according to claim 9 including electrical insulation disposed between said extensions upon securement of the components to one another, each bypass conduit including a pair of connections coupled to said semi-circular coil portions, respectively, and a flexible conduit portion coupled at opposite ends to said connections for flowing the cooling medium from one component to another of said components.

15. A tool according to claim 14 including a flexible conductive element extending between said coil portions for ensuring electrical conductivity between said coil portions.

16. A tool according to claim 9 wherein said components are pivotal relative to one another adjacent said second ends affording a generally clamshell configuration.

* * * * *